United States Patent [19]
Wlodarczyk et al.

[11] Patent Number: 5,422,478
[45] Date of Patent: Jun. 6, 1995

[54] FIBEROPTIC PRESSURE SENSOR HAVING DRIFT CORRECTION MEANS FOR INSITU CALIBRATION

[75] Inventors: Marek T. Wlodarczyk, Birmingham; David O. Danielson, Chelsea, both of Mich.

[73] Assignee: Fiberoptic Sensor Technologies, Inc., Ann Arbor, Mich.

[21] Appl. No.: 314,613

[22] Filed: Sep. 28, 1994

Related U.S. Application Data

[63] Continuation of Ser. No. 121,182, Sep. 14, 1993, abandoned, which is a continuation-in-part of Ser. No. 870,395, Apr. 17, 1992, Pat. No. 5,247,171.

[51] Int. Cl.$^6$ .................................... H01J 40/14
[52] U.S. Cl. .......................... 250/227.21; 250/231.19; 128/634; 73/708
[58] Field of Search ............ 250/227.14, 227.19, 250/227.21, 231.10, 231.19; 385/12; 73/705, 708, 722, 728; 128/634, 673, 675, 665, 667, 748

[56] References Cited

U.S. PATENT DOCUMENTS

| | | | |
|---|---|---|---|
| 4,453,218 | 6/1984 | Sperinde et al. | 364/416 |
| 4,678,902 | 7/1987 | Perlin | 250/227 |
| 4,711,246 | 12/1987 | Alderson | 128/667 |
| 4,787,396 | 11/1988 | Pidorenko | 128/667 |
| 4,856,317 | 8/1989 | Pidorenko et al. | 73/4 R |
| 4,886,070 | 12/1989 | Demarest | 128/667 |
| 4,924,870 | 5/1990 | Wlodarczyk et al. | 128/667 |
| 4,991,590 | 2/1991 | Shi | 128/667 |
| 5,018,529 | 5/1991 | Tenerz et al. | 128/667 |
| 5,048,524 | 9/1991 | Bailey | 128/634 |
| 5,146,083 | 9/1992 | Zuckerwar et al. | 250/227.21 |
| 5,247,171 | 9/1993 | Wlodarczyk et al. | 250/227.21 |
| 5,275,053 | 1/1994 | Wlodarczyk et al. | 73/705 |
| 5,280,786 | 1/1994 | Wlodarczyk et al. | 128/634 |
| 5,367,583 | 11/1994 | Sirkis | 250/227.19 |

*Primary Examiner*—David C. Nelms
*Assistant Examiner*—John R. Lee
*Attorney, Agent, or Firm*—Harness, Dickey & Pierce

[57] ABSTRACT

An improved intensity-encoded fiber optic sensor incorporating novel drift correction and filtering means is disclosed. The first embodiments of the invention relate to means for removing unwanted higher-order core and cladding modes from an intensity-encoded signal in an optical fiber using mode strippers and mode filters located strategically at various points in the sensing system. The second set of improvements in the invention relate to an improved technique for long-term temporal drift cancellation in a fiber optic pressure sensor by periodically applying pressure to the sensor tip in order to ascertain the measured voltage at which the sensor diaphragm contacts other elements of the sensor. This measured voltage is subtracted from an initial calibration voltage, and the result is applied to the measured signal as a constant correction term.

9 Claims, 10 Drawing Sheets

FIBEROPTIC PRESSURE SENSOR HAVING DRIFT CORRECTION MEANS FOR INSITU CALIBRATION

This application is a continuation of U.S. patent application Ser. No. 08/121/182, filed Sep. 14, 1993, now abandoned, which is a continuation-in-part of U.S. application Ser. No. 07/870,395, filed on Apr. 17, 1992, now U.S. Pat. No. 5,247,171.

BACKGROUND AND SUMMARY OF THE INVENTION

This invention relates to improvements in fiber optic sensor systems, and in particular, to techniques for reducing bending and connector instabilities in intensity-encoded fiber optic sensors, as well as temporal drift correction for fiber optic pressure sensors.

Optical fiber sensing systems have found applications in many environments. For example, the measurement of intravascular blood pressure of human patients has been accomplished using equipment manufactured by the present Assignee, FiberOptic Sensor Technologies, Inc. (FST), in which a diaphragm at the fiber sensing tip deforms in response to a pressure differential, thus modulating through reflection the light signals sent through the fiber. Changes in the distance between a deformed diaphragm and the optical fiber end, and the diaphragm shape, modulate the amplitude of light that is reflected back into the optical fiber. Accordingly, the intensity of the returned light signal is related to the pressure acting on the sensing tip.

Applicant has made numerous advancements in the technology of fiber optic sensing systems which are principally oriented toward pressure measurement. The present Assignee, FST, also owns U.S. Pat. Nos. 4,711,246, 4,787,396 and 4,924,870, as well as copending applications with Ser. No. 748,082, now U.S. Pat. No. 5,275,053, and Ser. No. 823,143, now U.S. Pat. No. 5,280,786, which are related to various improvements in fiber optic sensors and which are hereby incorporated by reference.

While the systems in accordance with these prior patents and applications provide excellent performance for the intended applications, Applicant is seeking to minimize errors introduced in the measurement of physical parameters by bending and connector instabilities, as well as to minimize error introduced by drift over long periods of time in the sensing system.

Two common sources of error in the measurement of physical parameters by intensity-encoded fiber optic sensors are bending and connector instabilities. These errors are particularly significant for higher-order and cladding light transmission modes, which are often the dominant modes of propagation in short fibers, where a steady-state mode distribution has not yet been achieved. Bending instabilities arise because the local critical angle in an optical fiber varies with the fiber's bending radius, so that higher-order modes, with initial angles of incidence nearly equal to the critical angle, will pass out of a bent fiber but not a straight one. Similarly, connector instabilities, which result from imperfect alignment between the transmitting and receiving fibers, have a large effect on signal attenuation in short fibers by erratically transforming the mode distribution within the receiving fiber, with the result that axial modes in the transmitting fiber may become higher-order modes in the receiving fiber and vice versa. Typically, a two-centimeter bend in a 100-micron fiber may result in up to several percentage points of change in transmitted intensity. In addition to the above-mentioned sources of error, other time-dependent errors may be introduced by temperature-induced changes in fiber transmissivity.

The present invention seeks to minimize these sources of error by using specially-placed mode filters and strippers to filter the transmitted and received light signals to remove most cladding and higher-order core modes. The first-mentioned embodiment of the present invention employs mode strippers and mode filters to remove unwanted higher-order core and cladding modes. Mode filters consist of a fiber deformer which forms periodic bends in the encapsulated optical fiber. The periodic bends in the fiber, usually having radii of curvature on the order of several millimeters, remove the unwanted higher-order modes by effectively varying the incident angle of light passing through the fiber in parts of the bends, allowing many of the higher-order modes to simply pass through the fiber rather than undergo total internal reflection. Mode strippers rely on a cladding doped with an optically-opaque material over a short distance to remove modes which propagate in the fiber's cladding.

While mode strippers and filters are well known in the art, the first embodiment of the present invention selectively places them in a novel fashion in the connectors between the sensor ferrule and the optical source, as well as in the sensor ferrule itself, to remove the unwanted higher-order core and cladding modes at the source of their generation. Another technique to reduce connector instabilities incorporated in embodiments of the present invention is the use of an angle polish on one of the optical fibers in the source-sensor connector. In this technique, one of the fibers is cut at an angle to its normal, while the other end of the fiber remains flat. The angle polish, when applied to one of the fibers, ensures that both fibers sought to be connected will remain separated by more than a quarter wavelength over most of their faces, thus preventing unwanted interference effects from reflections at both fiber ends. Such an angle polish also acts as a filter for removing some additional higher-order modes in the source fiber.

Another important technique of the present invention for reducing errors associated with bending, connector, and time-varying transmissivity instabilities in pressure-measuring sensors consists of periodically recalibrating the sensor by externally applying a pressure differential to the sensing diaphragm sufficient to cause the diaphragm to contact protrusions placed on the sensor ferrule. The difference of the system voltage obtained during each recalibration, which is proportional to the reflected light intensity recorded by photodetectors, and the system voltage recorded during an initial calibration run, is subtracted from the measured system voltage as a constant correction term. In a first embodiment for drift correction according to this invention, to facilitate identification of the contact event, the tip of the sensor ferrule is provided with one or more protrusions which contact the diaphragm during the recalibration event. This contact event may be identified by the signal-processing apparatus by either lock-in detection, autocorrelation, or averaging techniques. The first of these relies on the superposition of a high-frequency pressure signal with an associated dither frequency on the vacuum ramp applied to the diaphragm during the calibration operation; the signal processing apparatus examines the component of the voltage at the selected frequency, and observes the contact event as a change in signal amplitude at that frequency. The autocorrelation technique compares two temporally-successive pressure waveforms for significant changes; the contact event is identified when the second differs materially in functional form from the first. The final technique relies on averaging the measured system voltage values derived during calibration over pressure, identifying the contact event and associated correction term when the standard deviation in the averaged voltage values drops below a preselected number.

Because the accuracy of determining contact voltage depends critically on the uniqueness and repeatability of the voltage signature associated with the contact event, the signature is substantially affected by the shape of the fiber ferrule surface. In a second embodiment for drift correction according to this invention, a fiber optic ferrule is angle polished with respect to the ferrule axis in order to create a mechanical stop where the ferrule contacts the diaphragm. The mechanical stop provides a reference within the sensor which is unchanging whether the sensor is located externally or insitu. During initial calibration, when the diaphragm contacts the mechanical stop the catheter signal is stored for later use. During insitu correction, when the diaphragm contacts the mechanical stop, the catheter signal is again measured. The difference between the optical fiber output signal when the diaphragm contacts the mechanical stop during external calibration and insitu calibration is indicative of an error value used to correct the catheter signal. Contact between the diaphragm and the ferrule is indicated by a maximum voltage output by the sensor. This method enables correction for drift induced by temperature, stress on the optical fiber, and mechanical drift within the optical fiber. Furthermore, such a method is also useful for the correction of horizontal or vertical shift in pressure bleed curves as well as a change in shape in the pressure bleed curve, defined as a gain change, typically resulting from temperature variations. A range of correction values may be used to modify the voltage-pressure relation table by adding or subtracting correction values to the original calibration values.

Additional benefits and advantages of the present invention will become apparent to those skilled in the art to which this invention relates from the subsequent description of the preferred embodiments and the appended claims, taken in conjunction with the accompanying drawings.

DESCRIPTION OF THE DRAWINGS

FIG. 17 is a graph of sensed voltage versus applied vacuum pressure in which the contact event between the angle polished ferrule and the pressure sensing diaphragm is identified in accordance with the maximum output voltage; and.

DETAILED DESCRIPTION OF THE INVENTION

This invention is directed to two areas of improvement in intensity-modulated fiber optic sensing systems. For the sake of clarity, the various aspects of this invention will be discussed in separate sections identified by descriptive headings.

In-fiber Correction of Connector and Bending Instabilities

Figure 1:
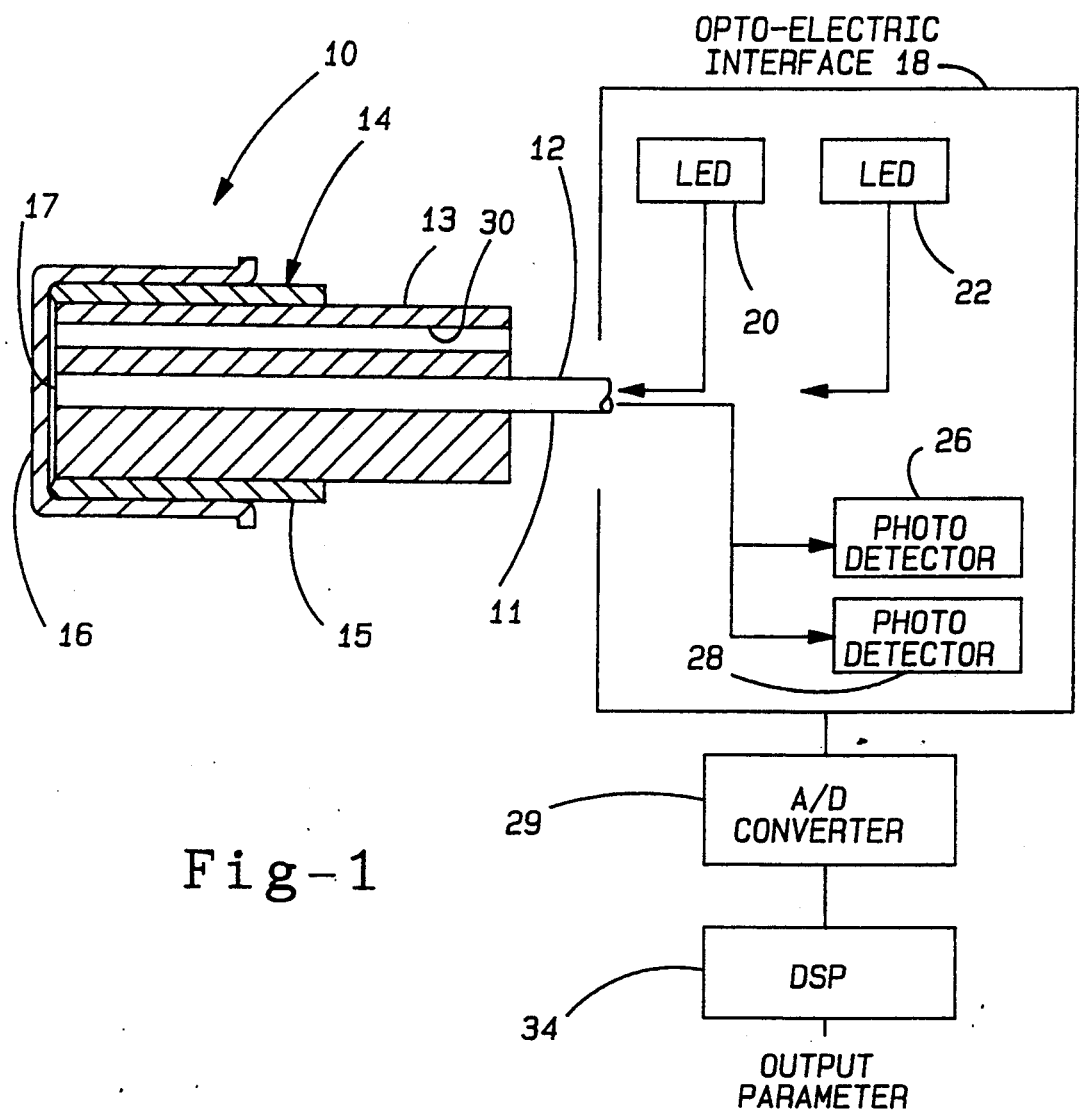
FIG. 1 is a block diagram of a system sensing a chosen physical parameter in accordance with the present invention.

A generalized fiber optic sensing system is shown in FIG. 1 and is generally designated there by reference number 10. System 10 includes fiber optic cable 12 which has a sensing tip 14 at its terminal end. Optical fiber 11 passes through ferrule 13 to which it is bonded or interference fit. Cylinder 15 surrounds ferrule 13. Deflectable diaphragm cap 16 has a center membrane portion which deforms in response to pressure differentials across it, and thus changes the amplitude of light launched into optical filament 11 at the opposite end of the filament which is returned back into the filament. For the purposes of illustration, pressure has been chosen to be the physical parameter to be measured by the fiber optic sensor, but the in-fiber correction scheme of the present invention will work equally well for any physical parameter sought to be measured by an intensity-encoded fiber-optic sensing system. A vent passage 30 is provided to maintain the fiber side of the diaphragm cap 16 at a desired pressure during in situ measurement or calibration. A partially reflective dielectric filter 17, comprised of numerous layers of dielectric material, for example titanium dioxide or silicon dioxide, is deposited on the end of filament 11 and provides a dual wavelength referencing feature such as that described in applicant's previously-issued U.S. Pat. No. 4,924,870. The features of this invention are also applicable to sensing systems which do not employ these wavelength referencing features, however.

Opto-electronic interface 18 contains the optical sources, LEDs 20 and 22, each emitting light in distinct wavelength bands; photodetectors 26 and 28; and a coupler, not shown, for launching light from the LEDs into optical filament 11 and directing the returned signals to be incident on the photodetectors. Some of the light from the LEDs is directed to fall on photodetector 26, which provides a source intensity reference. The output signals from opto-electronic interface 18 are converted into digital form by A/D converter 29 and transmitted to digital signal processing (DSP) module 34. The two signals are related to the intensity of the returned signals of the two LEDs. DSP module 34 and the associated host microprocessor control the operation of LEDs 20 and 22 and perform real-time computations and conversions. The outputs of module 34 are real-time readings of the physical parameter chosen, in this case pressure.

The deflection of the diaphragm cap 16 is measured using the dual-wavelength reference technique described in U.S. Pat. No. 4,924,870, in which the light signal from LED 20 is reflected by filter layer 17, whereas the light pulse from LED 22 passes through the filter to be modulated by diaphragm cap 16. The use of the referencing wavelength from LED 20 in this approach permits some compensation for environmental effects on the system such as vibration, connector instability, bending effects, and some of the sensing tip irregularities.

Figure 2:
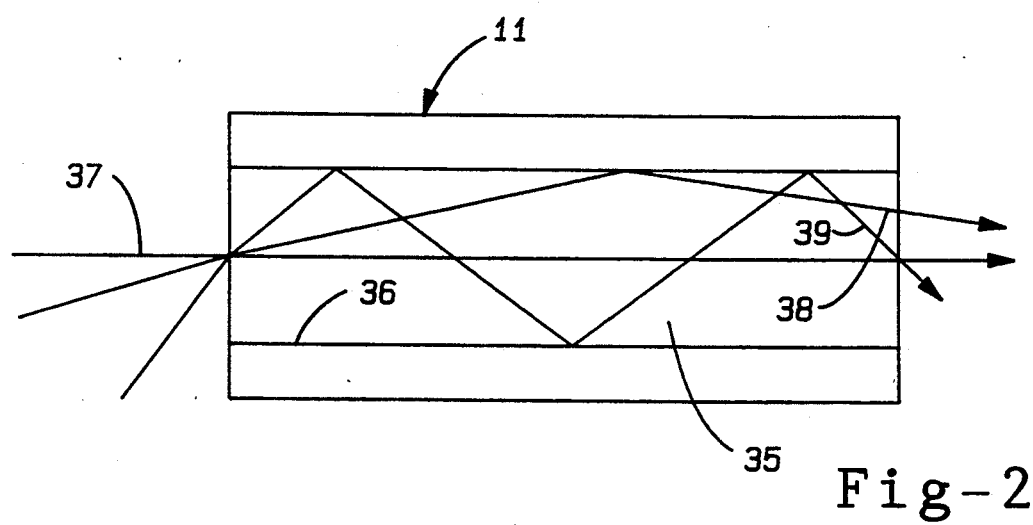
FIG. 2 is a cross-section of a stepped-index optical fiber showing in diagrammatic form various modes of light propagation through the optical fiber relevant to the present invention.

FIG. 2 shows an optical fiber used in the present invention to convey intensity-encoded light signals from opto-electronic interface 18 to sensing tip 14. The fiber consists of two different optical materials, a core 35 and a cladding 36, having different indices of refraction. The cladding's index of refraction is chosen to be lower than the core's to facilitate the total internal reflection of most of the light propagating within the fiber. Since the diameter of the optical fiber is considerably greater than the wavelength of the relevant light, many different propagation conditions (modes) are possible within the fiber. Three such propagation conditions, axial modes 37, which propagate straight through the fiber while undergoing very few or no reflections, low-order modes 38, which are characterized by a small launching angle and relatively few reflections per unit length, and high-order modes 39, characterized by a high launching angle into the fiber and a relatively large number of reflections per unit length, are particularly important for the purposes of the present invention. Due to their relatively large launching angles, which approach the critical angle of the optical fiber in many cases, the transmitted intensity of high-order modes is affected by the bending of optical fiber 11 to a much greater extent than that of the low-order and axial modes. Such bending of optical fiber 11 locally varies the incident angle of many of these high-order modes 39 sufficiently to allow them to exceed the fiber's critical angle and escape the fiber core entirely after a few partial reflections. The presence of a significant fraction of high-order modes in the reflected signal and the consequent loss of many of these modes thus makes the total intensity of the signal reflected from sensing tip 14 strongly dependent on fiber bending conditions. The correction apparatus of the present invention therefore seeks to remove most of the high-order modes from optical fiber 11. While a stepped-index fiber has been chosen for the purposes of illustration, it should be kept in mind that the discussion also applies to a graded-index fiber incorporating a core with a variable index of refraction.

Figure 3:
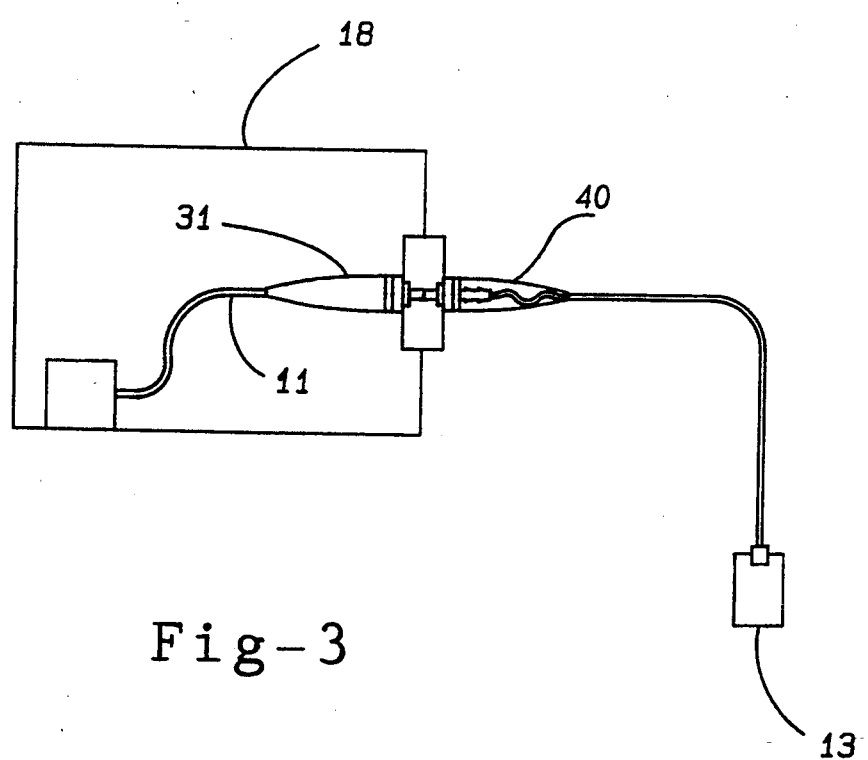
FIG. 3 is a schematic diagram showing the position of a fiber connector of the present invention incorporating an integral mode filter.

FIG. 3 is a schematic diagram showing one possible placement of the in-line connectors in a fiber optic sensor of the present invention. Opto-electronic interface 18 contains an in-line connector 31 housing optical fiber 11, which mates with another in-line connector 40, containing optical fiber 11 and connected to ferrule 13.

Figure 4:
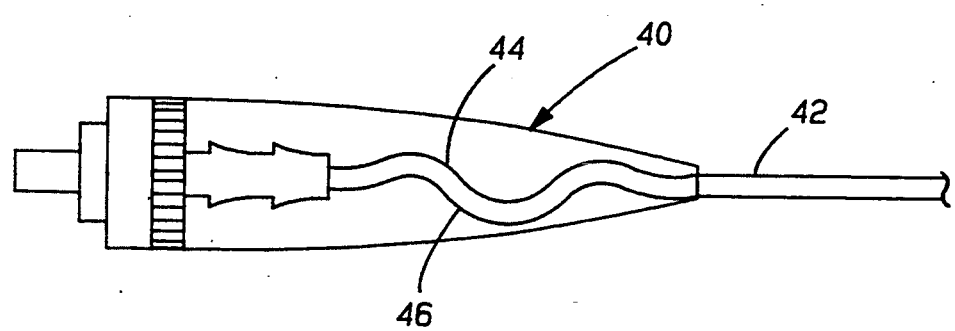
FIG. 4 is a cross-section of a fiber connector of the present invention.

A connector 40 incorporating an integral mode filter of the present invention is shown in FIG. 4. Connector 40, a conventional fiber connector, contains an optical fiber 42 in its center and can be plugged into a similar fiber connector containing a second optical fiber to optically couple the fibers, as shown in FIG. 3. Connector 40 incorporates an integral mode filter 44 within its body. Mode filter 44 consists of an element which periodically deforms center fiber 42, such as a plastic or metal tube incorporating a periodic set of bends. This tube completely encloses center fiber 42, causing it to assume the periodic bend form itself. The periodic bends 46 in mode filter 44 vary the angle of incidence for light reaching the outer interface of the fiber core 35 at these bends 46, and all modes propagating in the fiber with an angle greater than the fiber's critical angle will be transmitted out of the fiber within a few reflections rather than undergo total internal reflection and continue propagation. Since these bends locally increase the angle of incidence of light striking the outside of the fiber core 35 at certain points in the fiber, the periodic bends 46 result in differentially greater attenuation of higher-order modes, since the angles of incidence for these modes are closer to the critical angle before reaching the mode filter 44. Cladding modes, which are modes propagating within fiber cladding 36, are removed from the light signal in an analogous way by the bends 46 of the mode filter. The chosen number and radius of the bends 46 depend on empirical factors such as the fiber diameter, launching condition from sources 20 and 22, and the numerical aperture of the fiber. Bend radii of a few millimeters are generally satisfactory for fiber diameters on the order of 100 micrometers.

Figure 5:
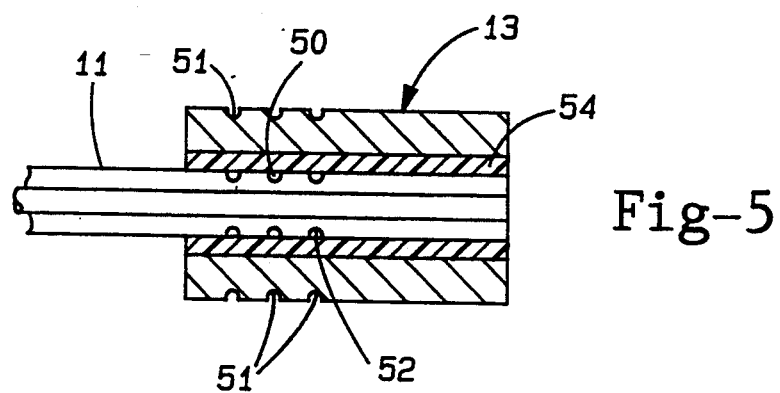
FIG. 5 is a cross-section of a mode stripper of the present invention incorporated at a sensor tip.

FIG. 5 illustrates a mode stripper and mode filter incorporated directly into the sensor tip of the fiber optic sensor. In-ferrule mode filter 50 is entirely contained within ferrule 13, as FIG. 5 shows. Ferrule 13 containing optical fiber 11 includes compression ridges 51, which periodically deform fiber 11 within ferrule 13, creating bends 52. These bends 52 act as a mode filter, varying the local incident angle of light within the fiber in a completely analogous way to that of bends 46 in mode filter 44 and differentially removing higher-order and cladding modes. An additional means to remove cladding modes is provided by a mode stripper 54, which is an approximately one-centimeter segment of cladding covered by a light-absorbing material, typically an epoxy which is optically black at the wavelengths used for the light signals. This mode stripper removes a substantial fraction of cladding modes through absorption.

Figure 6:
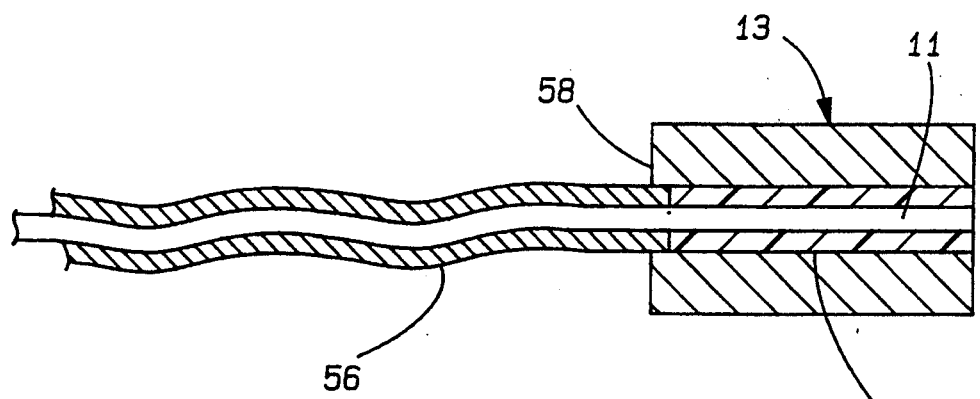
FIG. 6 is a cross-section of a mode filter adjacent to a sensor tip of the present invention.

A mode filter adjacent to sensor ferrule 13 is depicted in FIG. 6. Mode filter 56, consisting of a plastic or metal tube with periodic deformations, is connected to ferrule 13 at its rear face 58 and contains the portion of optical fiber 11 immediately adjacent to ferrule 13, deforming it periodically. The portion of optical fiber 11 contained in ferrule 13 contains a mode stripper 60, which is a one-centimeter length of fiber whose cladding is covered by an optically black epoxy, in an analogous way to that of mode stripper 54. Incorporation of mode filters 51 and 56 and mode strippers 54 and 60 into or adjacent the sensor ferrule 13 allows the mode filter to act on the incident light signal after all contributions to the mode distribution from fiber bending and connector instabilities in opto-electronic interface 18, connectors 31 and 40, and optical fiber 11 are already present immediately before the signal's reflection at diaphragm cap 16 and dielectric filter 17. Furthermore, reflection of the optical signal at diaphragm cap 16 also changes the signal's mode distribution, adding higher-order modes from nonparaxial reflections on the curved diaphragm. The mode filters 51 and 56 located within or adjacent to the sensor ferrule 13 strongly attenuate these reflected higher-order modes, preventing them from substantially altering the strength of the received light signal through differential bending losses in optical fiber 11. While it is important for ensuring adequate sensitivity of the received signal to diaphragm deflection that some nonaxial modes reach diaphragm cap 16 and undergo reflection, the mode filters of the present invention allow a substantial portion of low-order modes and a certain fraction of higher-order modes to pass through them.

Figure 7:
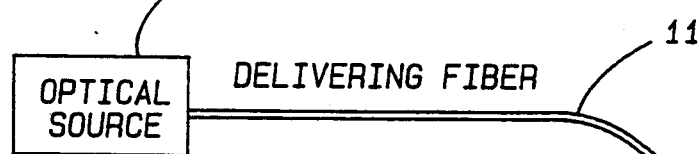
FIG. 7 is a schematic drawing showing the location of a mode filter in one embodiment of the present invention.
Figure 8:
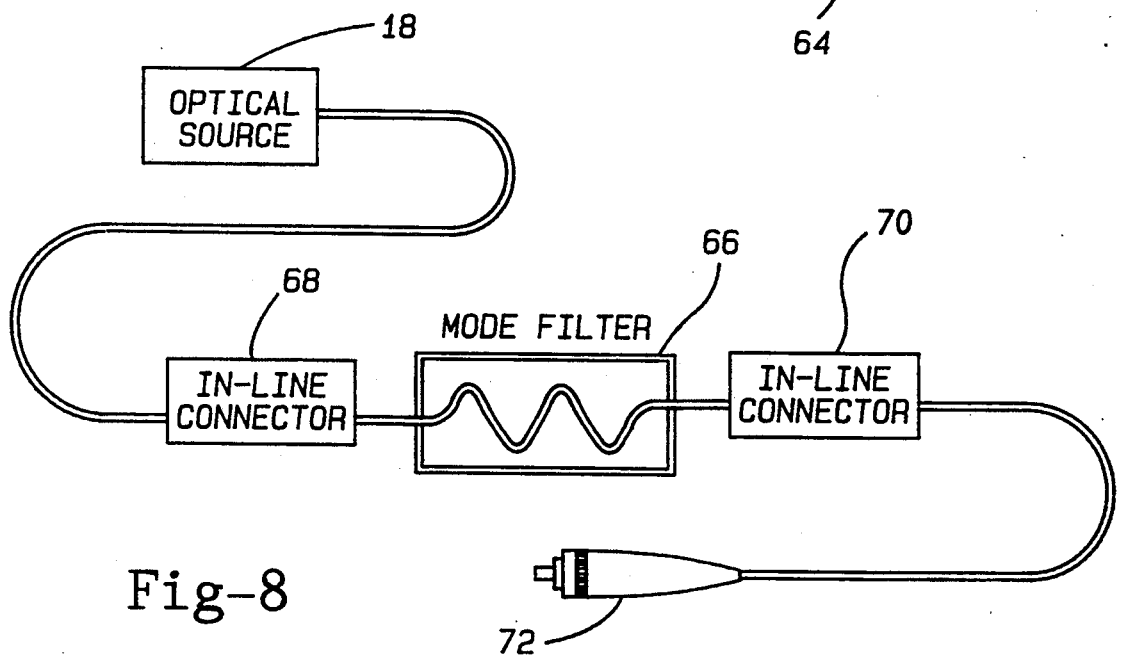
FIG. 8 is a schematic drawing showing the location of a mode filter in another embodiment of the present invention.

Additional locations for the placement of mode filters in fiber optic sensor 10 are shown in FIGS. 7 and 8. Referring to FIG. 7, mode filter 62 is incorporated into optical fiber 11 at a point between opto-electronic interface 18 and source connector 64, which connects to a similar connector containing a second length of fiber and the sensor ferrule, not shown. Placement of mode filter 62 in the location shown simplifies the design of ferrule 13 and allows thermal stabilization of mode filter 62 to eliminate temperature-induced drift in the sensing signal. The mode filter 66 shown in FIG. 8 is located on the source side of fiber optic sensor 10. Mode filter 66 is located between in-line connectors 68 and 70, which connect optical fiber 11 to connector 72, which joins a fourth connector, not shown, containing an optical fiber leading into sensor ferrule 13.

Figure 9:
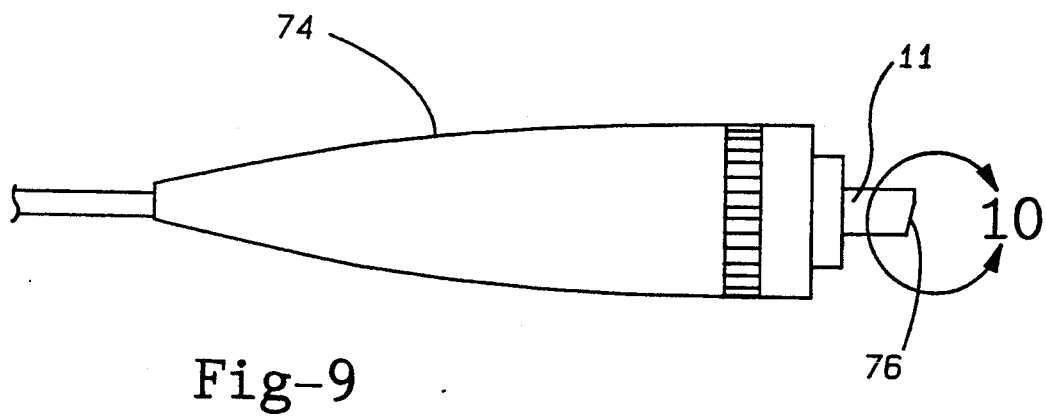
FIG. 9 is a cross-section of a fiber connector incorporating an angle polish of the present invention.
Figure 10:
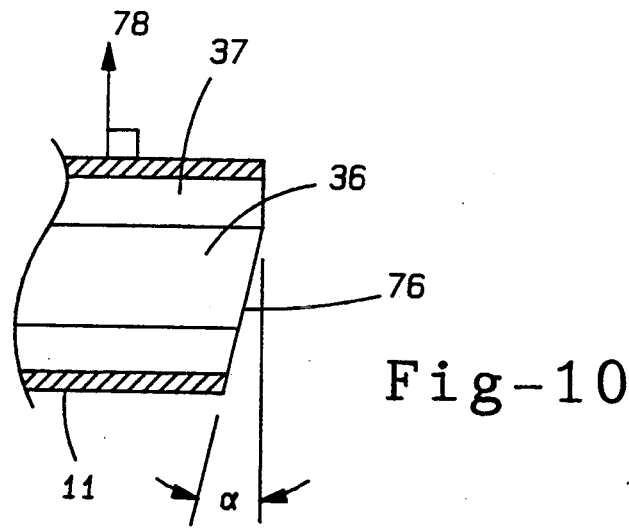
FIG. 10 is an enlargement of the cross-section of the fiber shown in FIG. 9 incorporating an angle polish of the present invention.
Figure 11:
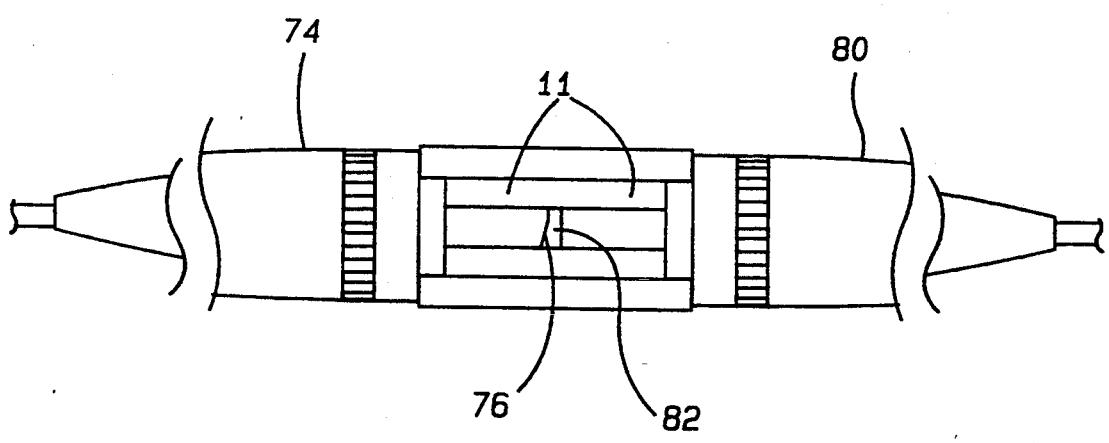
FIG. 11 is a cross-section showing the connection of two fiber connectors containing an angle polish of the present invention.

Another embodiment of the fiber optic sensor of the present invention contains an angle polish applied to optical fiber 11, as illustrated in FIGS. 9, 10, and 11. Edge 76 of optical fiber 11, contained in connector 74, is cut at an angle $\alpha$ to the fiber outer edge normal 78. The segment of optical fiber 11 contained in connector 74 joins a flat segment of fiber contained in another connector 80, forming a wedge-shaped gap 82 between the two fiber halves. Angle $\alpha$ is chosen to be the minimum angle compatible with a gap 82 having an average width greater than one-quarter of the wavelength of the light emitted from LEDs 20 and 22. Such a requirement results in values for $\alpha$ of approximately 5 degrees. Gap 82 prevents undesirable interference effects from boundary reflections at the interfaces where the halves of optical fiber 11 join in connectors 74 and 80. Although the use of an angle polish in fiber connectors is known, these prior art angle polishes have been used to minimize specular reflections between fibers rather than prevent unwanted interference effects; consequently, the angle $\alpha$ chosen for these prior-art polishes has normally been approximately 10 degrees or greater rather than the small values used in the present invention. The use of angles substantially greater than five degrees in the present invention would result in unacceptable losses from beam divergence as well as the introduction of unwanted higher-order modes into the light signal by off-axis refraction of the signal at angled surface 76.

Drift Correction using Periodic Recalibration

In addition to errors introduced into the sensing light signal by connector and bending instabilities, long-term temporal drift is a significant source of error in fiber optic systems. The inventors have found that the effects of many of these errors in fiber optic pressure sensors may be removed by periodically recalibrating the sensor by applying a time-varying pressure differential across the sensor's diaphragm to produce contact between the diaphragm and other parts of the sensor and using the signal level at the contact event to recalibrate the light signal. Since the contact event occurs at a particular pressure differential which remains constant during use, the intensity of reflected light signals at contact can be compared with prior values to produce a correction term.

Figure 12:
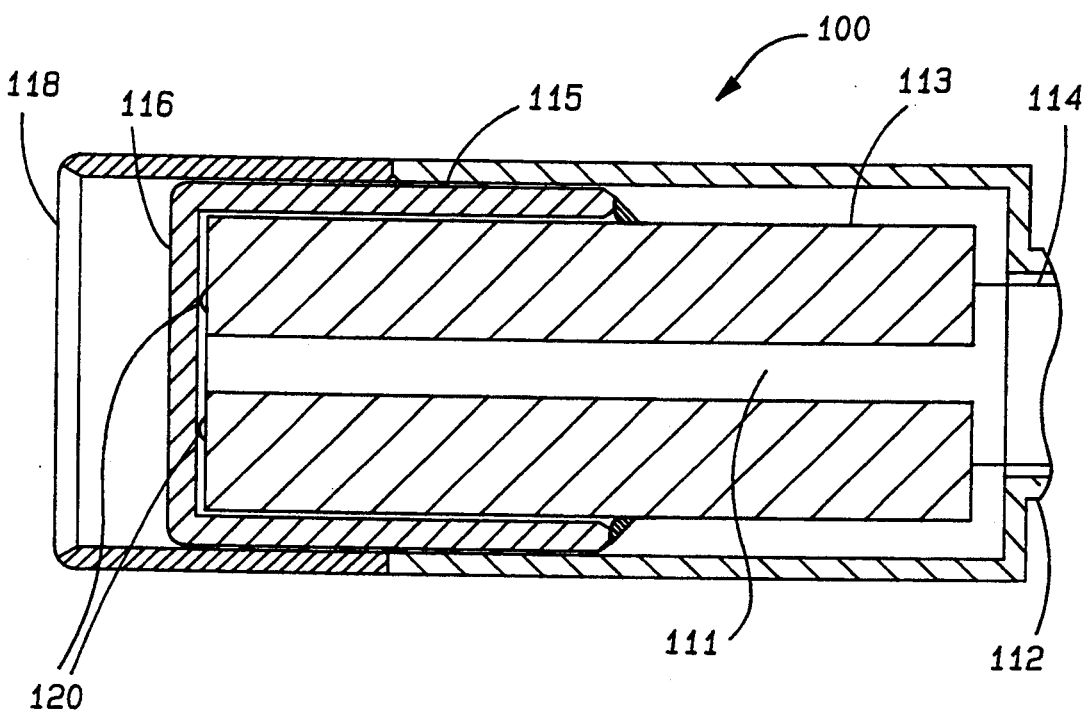
FIG. 12 is a cross-section of a sensing tip of yet another embodiment of the present invention containing two protrusions for engaging a pressure-sensing diaphragm.

A second sensing tip incorporating first embodiment of the present invention is shown in FIG. 12 at 100. Sensing tip 100 is connected to fiber optic cable 112, which contains optical fiber 111 and a vacuum passage 114 connected to a system vacuum port. Sensing tip 100 includes optical fiber 111, which passes through ferrule 113. Cylinder 115 partially surrounds ferrule 113. Deflectable diaphragm cap 116 has a membrane portion which deforms in response to pressure differentials across it, changing the amplitude of light launched into optical filament 111 which is returned back into the filament. A protective cover 118 protects diaphragm cap 116 and ferrule 113 from direct exposure to particles or other contaminants. Ferrule 113 also contains two small surface deformations 120 at its terminal end facing diaphragm cap 116.

Figure 13:
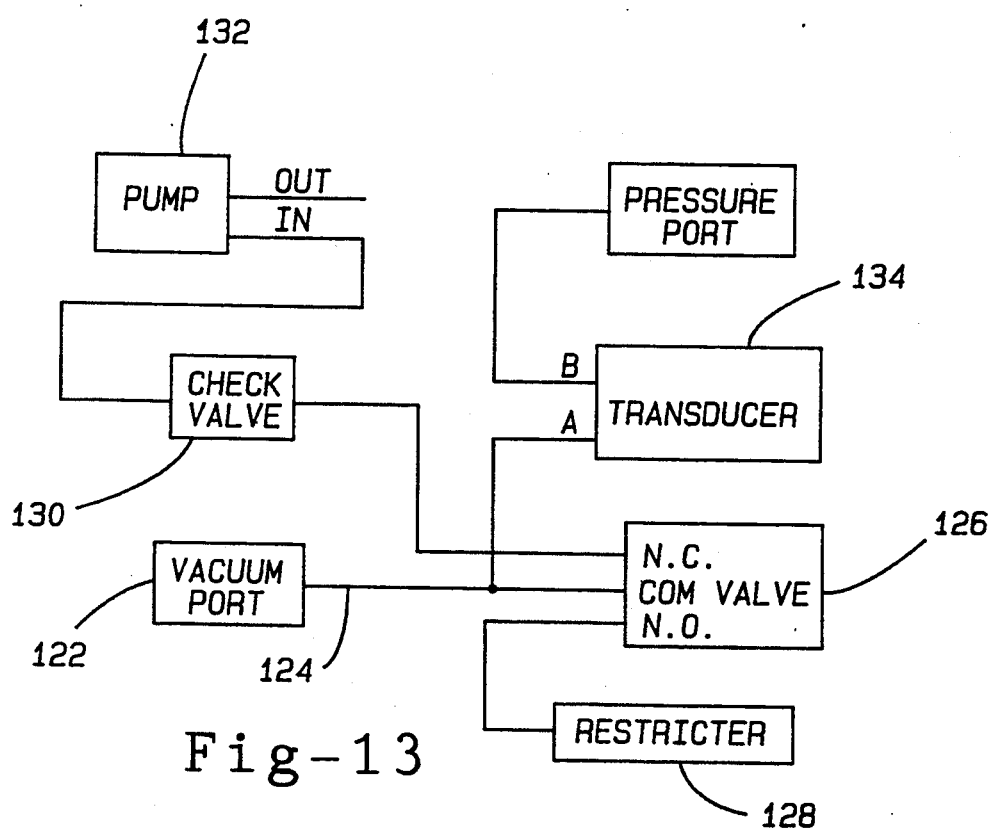
FIG. 13 is a schematic diagram showing the arrangement of the vacuum means of the present invention.

A plumbing schematic for the vacuum means in the fiber optic sensor is shown in FIG. 13. One end of vacuum port 122 is connected to vacuum passage 114, which communicates with sensor ferrule 113 and the inner surface of diaphragm 116 facing the ferrule. The other end of vacuum port 122 is connected to vacuum line 124, which is connected to control valve 126. Control valve 126 allows vacuum port 122 to communicate with restricter 128, check valve 130 and vacuum pump 132. Transducer 134 is connected across and measures the vacuum pressure in line 124. Vacuum pump 132 draws a vacuum on vacuum port 122 through check valve 130 and control valve 126. Check valve 130 acts as a volume reservoir, allowing the entire vacuum system and fiber optic sensor tip 100 to be maintained at an almost constant pressure over a desired sample time interval.

The drift correction system operates by applying a time-varying level of vacuum through pump 132, check valve 130, control valve 126, vacuum port 122, and vacuum passage 114, to the inner surface of diaphragm cap 116. This vacuum causes diaphragm cap 116 to be displaced toward and eventually contact surface protrusions 120. It is important to note that although the physiological pressure waveform acting on the outer surface of diaphragm 116 is constantly changing and cannot be exactly measured during the calibration event, diaphragm 116 will always contact surface deformations 120 at a fixed pressure differential between the outer and inner surfaces. It is therefore unnecessary to exactly know the pressure being applied to the diaphragm's outer surface, since the contact event produces an identifiable voltage signature and indicates a constant, reference pressure differential between the two surfaces. Surface protrusions 120 serve the important purpose of preventing diaphragm cap 116 from contacting the surface of ferrule 113; allowing it to do so would create undesirable interference effects in the returned optical signal. Furthermore, the protrusions 120 must be made of a hard material in order to remain dimensionally stable through repeated calibration procedures.

The invention accomplishes drift correction by activating the vacuum pump either periodically or on demand from the operator. The frequency of on-demand recalibration is strongly dependent on the desired accuracy in the system as well as the degree of accuracy with which the contact voltage $V_c$ can be determined. In general, the lower the desired level of accuracy and the less accurately $V_c$ can be determined by DSP 34, the less frequently the user will wish to perform recalibration. The recalibration operation results in the generation of a time-varying system error term $V_e$, which is subtracted from all subsequent values of the measured signal until the next recalibration to produce an output signal voltage $V_{out}$ satisfying $$V_{out}(t) = V_m(t) - V_e(T) \qquad (1)$$

where $V_m(t)$ is the measured value for voltage at time t. $V_e$ itself is updated at each recalibration (at t=T) by comparing the contact voltage value $V_c$ at an initial calibration run (t=0) to that at t=T according to $$V_e(T) = V_c(T) - V_c(0) \qquad (2)$$

where $V_c(0)$ is the value of the voltage signal at the contact event derived from an initial calibration.

Figure 14:
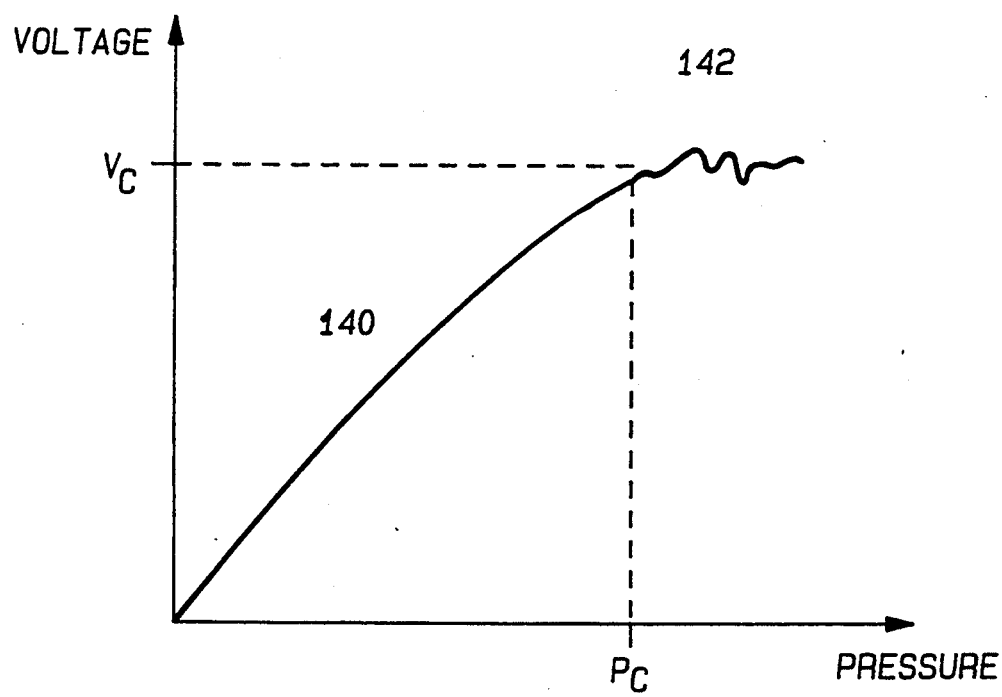
FIG. 14 is a graph of sensed voltage versus applied vacuum pressure showing the characteristic signature of a contact event relied on in one embodiment of the present invention in identifying a contact event between the sensing tip's diaphragm and the protrusions in the sensor tip.

This contact event produces a characteristic waveform signature which can be identified by the sensor's signal processing apparatus in one of several ways. FIG. 14 shows a typical relationship between pressure and output voltage $V_m$ from A/D converter 29. In FIG. 14, signal measured voltage is indicated on the vertical axis, while differential pressure across diaphragm cap 16 is indicated on the horizontal axis. Graph 140 shows the functional form of the output signal. Contact of diaphragm cap 16 with protrusions 120 is clearly indicated on the graph at $(V_c, p_c)$; the characteristic form of the output signal at $(V_c, p_c)$ is shown at 142.

A technique relied on by the signal processing apparatus in one embodiment of the present invention to determine the contact event is lock-in detection. The lock-in detection method involves applying a vacuum to the inner surface of diaphragm 116 which has the functional form of a linear ramp in pressure and time with a superimposed high-frequency dither. The frequency of the superimposed waveform must be chosen to be above the physiological frequencies of interest in the system to minimize physiological noise. A lock-in amplifier in DSP 34 operates on the output voltage signal from A/D converter 29. This lock-in amplifier examines the component of the voltage signal from the reflected light at the dithering frequency for large amplitude changes. Because the contact event produces a large amplitude change in the component of the returned signal at the dithering frequency, the lock-in amplifier identifies the contact event by its identification of a large amplitude change at that frequency. The associated output signal and pressure values $V_c$ and $P_c$ associated with the contact event are simply those indicated by A/D converter 29 and pressure transducer 134 at the contact event. If a relatively long time interval is used between successive recalibrations, the lock-in detection may be performed several times and the average value of the contact voltage and pressure may be used to obtain a more accurate correction.

A second technique for detecting the contact event involves the use of waveform comparison. This technique involves the application of a vacuum by pump 132 to the inner surface of diaphragm cap 116; as this vacuum is being applied, DSP apparatus 34 stores two successive output waveforms over a chosen sample interval; an autocorrelation apparatus compares the successive waveforms by a technique such as subtracting one from the other to form a difference function or using a correlation function such as $$\phi_{ar}(\tau) = \sum_t a_t r_{t+\tau} \qquad (3)$$

where $a_t$ is the time-series representation of the first waveform and $r_t$ is the time-series representation of the second waveform. The function $\phi_{ar}$ $\phi_{ar}$ measures the functional similarity of the two waveforms as a function of time shift $v$; if $\phi_{ar}$ is suitably normalized, $\phi_{ar}(0)$ will become quite small at the contact event as the two waveforms become more and more dissimilar. In the absence of a contact event, successive pressure waveforms will have approximately the same functional form since their underlying physiological components are roughly invariant if the sample interval is chosen to be long enough. At the contact event, however, the sudden change in the waveform, as indicated at 142, will cause the two stored waveforms to appreciably differ, and the autocorrelation unit will identify this difference and thereby detect the contact event, providing a value for $V_c$ for use in the error equation.

Figure 15:
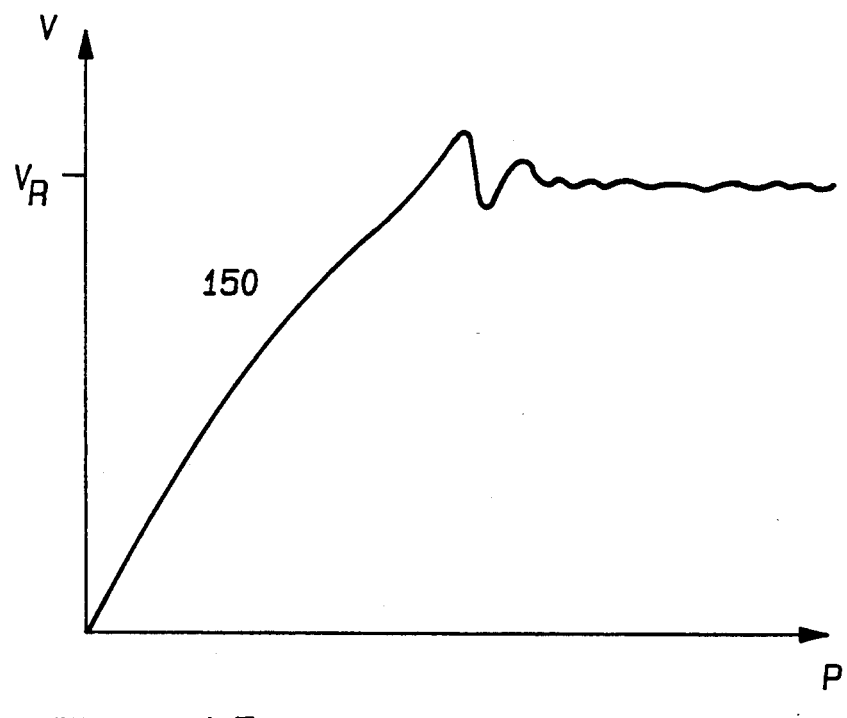
FIG. 15 is a graph of sensed voltage versus applied vacuum pressure showing a second method employed in the present invention of identifying a contact event between the sensing tip's diaphragm and the protrusions.

A third technique for detecting the contact event involves the use of an averaging technique. Such a technique involves averaging successive voltage values over many applied pressures, as illustrated in FIG. 15, which is a graph of measured signal voltage for various values of applied pressure during the calibration operation. Averaging means in DSP module 34 averages successive values of $V_m$, which is plotted at 150, as increasing vacuum levels are applied by vacuum pump 132. After the contact event, it can be seen from FIG. 15 that the signal voltage flattens as a function of pressure; consequently, after enough values in the flat range of the curve have been included in the average, the standard deviation of the averaged voltage will drop below a predetermined cutoff value and the averaging apparatus will return $V_c$, the value of the signal voltage at the contact event. The resulting value of $V_c(T)$ is then used in the error equation to calculate $V_e(T)$ and subsequent values of $V_{out}$.

Insitu Calibration of the System

Figure 16:
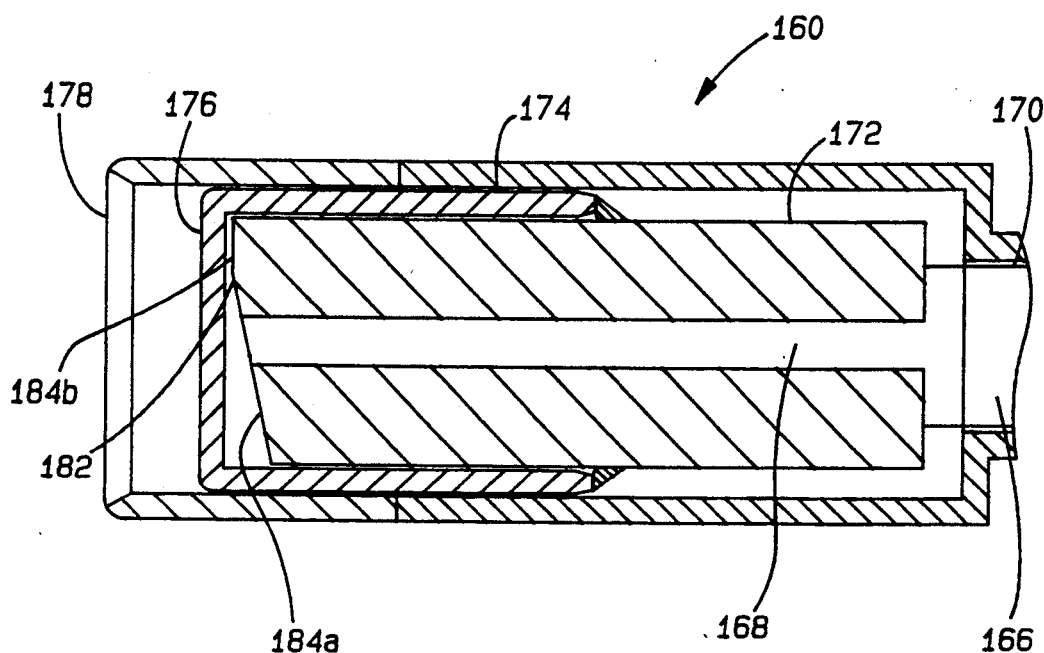
FIG. 16 is a cross-section of a sensing tip of yet another embodiment of the present invention in which the ferrule is angle polished at its end for engaging a pressure-sensing diaphragm.

In addition to the method and apparatus for calibration as described in the previous section, yet another sensing tip incorporating the first embodiment with the present invention is shown in FIG. 16 at 160. Sensing tip 160 depicted in FIG. 16 provides an apparatus for recalibrating the sensor in order to correct for drift resulting from temperature variation, stress on the optical fiber, and the mechanical drift within the sensing tip 160. Sensing tip 160 connects to fiber optic cable 166, which contains optical fiber 168 and a vacuum passage 170 connected to a system vacuum port. Optical fiber 168 passes through ferrule 172, and cylinder 174 partially surrounds ferrule 172. Deflectable diaphragm cap 176 has a membrane portion which deforms in response to pressure differentials across it, changing the amplitude of light launched into optical fiber 168 returned back into the optical fiber. A protective cover 178 protects diaphragm cap 176 and ferrule 172 from direct exposure to particles or other contaminants.

Ferrule 172 faces diaphragm cap 176 and is angle polished at its terminal end. At a sufficient pressure, diaphragm 176 deflects and contacts mechanical stop 182 which is defined as the line of intersection between the two polished end surfaces 184a and 184b. Because the mechanical stop 182 is on one side of optical fiber 168, diaphragm 176 is not supported evenly around optical fiber 168 when it contacts mechanical stop 182, though diaphragm 176 may still deform in accordance with changes in pressure. Deflection of diaphragm 176 after contact typically occurs at a much lower rate, and the diaphragm moves in a direction opposite that of optical fiber 168. Therefore, the point of contact represents a maximum catheter signal, and at pressures above the contact pressure, the catheter signal decreases, to yield a negative slope in a pressure versus catheter signal plot.

In describing the operation of the drift correction system, it should be noted that the plumbing schematic as defined in FIG. 13 may be used to apply vacuum pressure as well as to measure pressure, using pressure transducer 134. In a first step of the drift correction system, sensing tip 160 is initially calibrated when the external pressure upon a diaphragm is the atmospheric pressure (i.e., out of body). A time level varying of vacuum through pump 132, check valve 130, control valve 126, vacuum port 122 and vacuum passage 170 is applied to the inner surface of diaphragm cap 176. The vacuum causes diaphragm cap 176 to be displaced toward and eventually contact mechanical stop 182. Pressure transducer 134 of FIG. 13 measures vacuum pressure applied to vacuum passage 170, and a voltage output signal varying in accordance with the returned light is output by opto-electric interface 18 as depicted in FIG. 1. The opto-electric interface 18 of FIG. 1 is merely exemplary, and any interface providing an output signal in accordance with the returned light signal is equally applicable.

Figure 17:
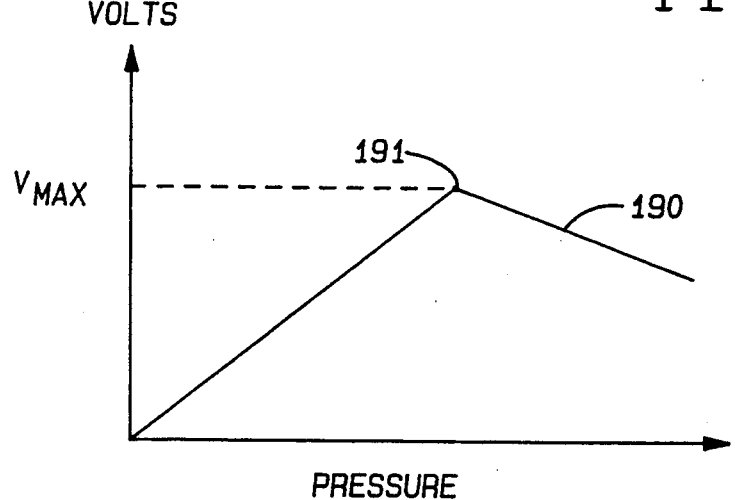
Figure 18:
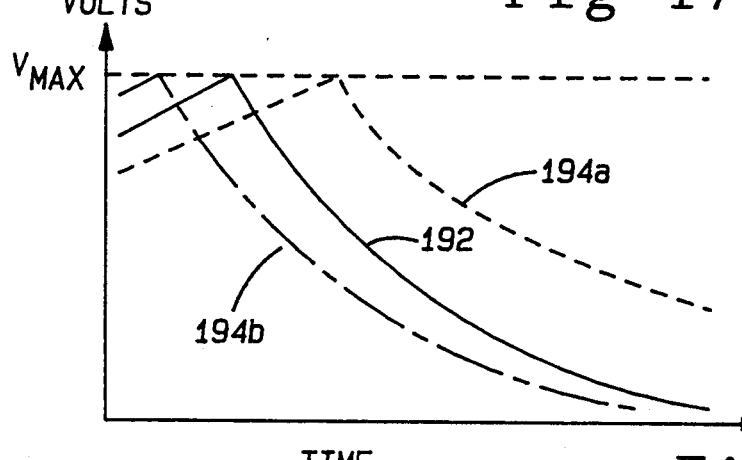
FIG. 18 is a graph of sensed voltage versus applied vacuum pressure in a typical non-calibrating operation mode according to yet another embodiment of the invention.

FIG. 17 depicts a waveform 190 of pressure exerted on diaphragm 176 versus returned catheter signal, where the returned catheter signal is measured in volts. As the pressure increases, the output voltage $V_{max}$ also increases until the output voltage reaches a maximum $V_{max}$ which corresponds to the contact point 191 between diaphragm 176 and mechanical stop 182. As vacuum pressure is further increased, the catheter signal decreases due to deformation of diaphragm 176 away from optical fiber 176. After the application of vacuum pressure, control valve 126 operates to allow air to bleed into the vacuum vent 170 so that the pressure may return to atmosphere. During this operation, the output voltage representing the returned light signal is periodically sampled so that a plot of voltage versus time for the bleed operation may be obtained. A typical plot depicting bleed curve 192 is shown in FIG. 18. The time component of the plot, shown along the x-axis, is typically measured by the number of data samples taken by an A/D converter, and the y-axis represents the returned light signal converted to volts.

Figure 19:
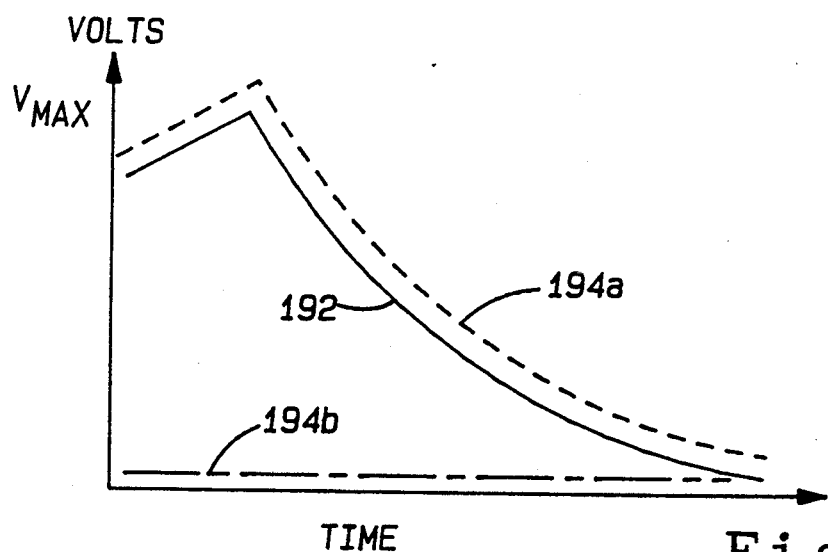
FIG. 19 shows the calibration bleed curve of FIG. 18 shifted upward.

Bleed curve 192 shown in FIG. 18 is referred to as the calibration bleed curve. When sensor tip 160 is located within the body, insitu, the bleed curve may vary in a number of ways. If the external pressure is applied to fiber optic sensor tip 160, the calibration bleed curve 192 will shift left or right depending on whether the pressure is a positive external pressure (right shift) as shown in bleed curve 194a or a negative external pressure (left shift) as shown in bleed curve 194b. Such a left-right shift is a result of either more time being required to equal the external pressure (positive pressure) or less time being required to equalize the external pressure (negative pressure). The calibration curve depicted in FIG. 18 may also shift up or down along the y-axis in accordance with drift generally caused by stress on the optical fiber as shown in FIG. 19. FIG. 19 shows the calibration bleed curve 192 of FIG. 18 shifted upward as bleed curve 196. A vertical shift generally corresponds to a constant error signal 198 caused by stress, and may be compensated by shifting an insitu calibration curve, to be described herein, by a constant term corresponding to the magnitude of the error signal 198.

Figure 20:
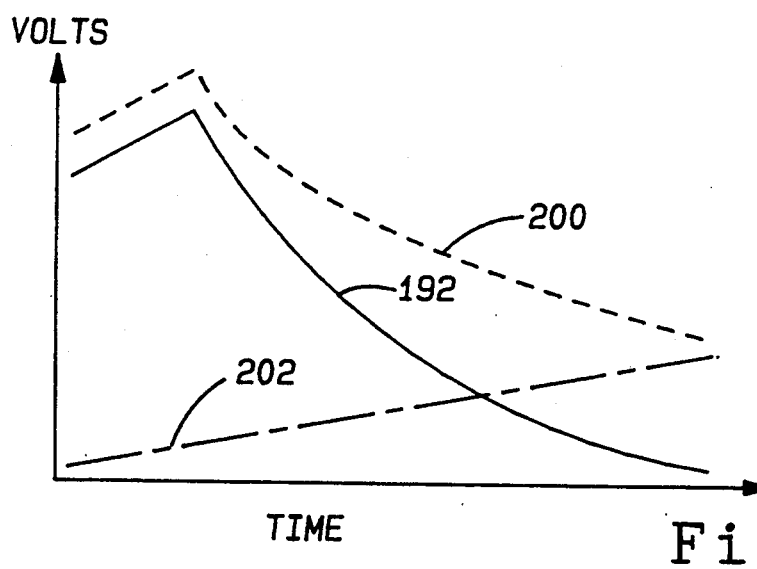
FIG. 20 shows an insitu bleed curve exhibiting environmental temperature variations affecting the sensor tip.
Figure 21:
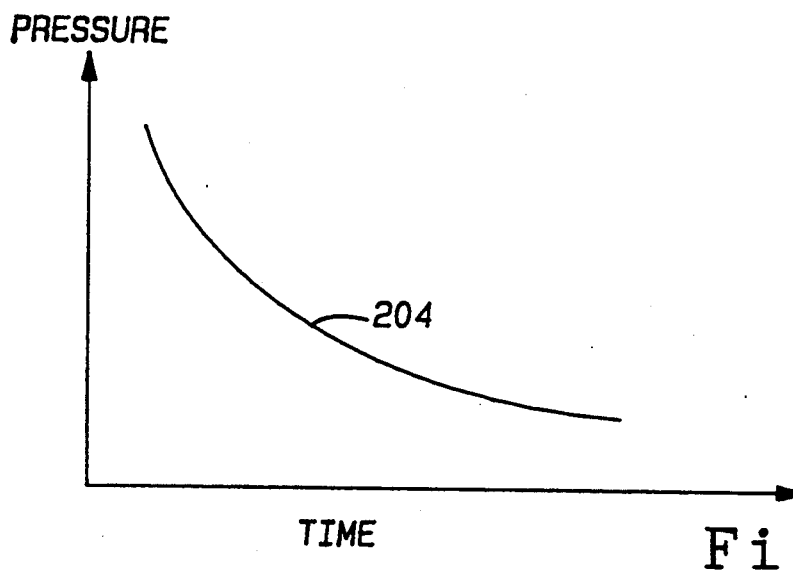
FIG. 21 shows the pressure change as air bleeds back into the vacuum vent of the sensor tip.

As shown in FIG. 20, the insitu bleed curve 192 of FIG. 20 may also vary in shape as demonstrated by insitu bleed curve 200. These changes are typically the result of temperature variations of the environment in which sensor tip 160 operates. Such temperature changes are responsible for both vertical shift in the insitu bleed curve as well as changes in shape of bleed curve 192. Changes in shape of bleed curve 192 are generally referred to as gain changes and are compensated for using error terms other than merely a constant correction term as is demonstrated in curve 202. In order to correct for the aforementioned gain chance, it is useful to understand the difference between the calibration bleed curve 192 and insitu bleed curve 200. After control valve 126 has been opened and while air bleeds back into vacuum vent 170, the pressure change as measured by pressure transducer 134 is exponential as is demonstrated in waveform 204 of FIG. 21. The pressure actually increases from a negative value, but is shown positive for easier comparison to the calibration curves as discussed above. The returned signal is an exponential signal modified by the output versus pressure curve as shown in FIG. 17. If the data were converted from a catheter output signal (voltage) to an actual pressure, it would be an exponential. This conversion may be accomplished by substituting pressure values for catheter signal (voltage) values of waveform 200 using the catheter calibration curve 192 as depicted in FIG. 18. If an insitu bleed curve and the calibration bleed curve are converted to an exponential pressure change, the difference between them is a constant pressure plus an error. If the constant pressure can be determined and subtracted from the insitu bleed curve, the remaining data is the error. Once the error curve is known, it may be used to correct the catheter signal.

Figure 22:
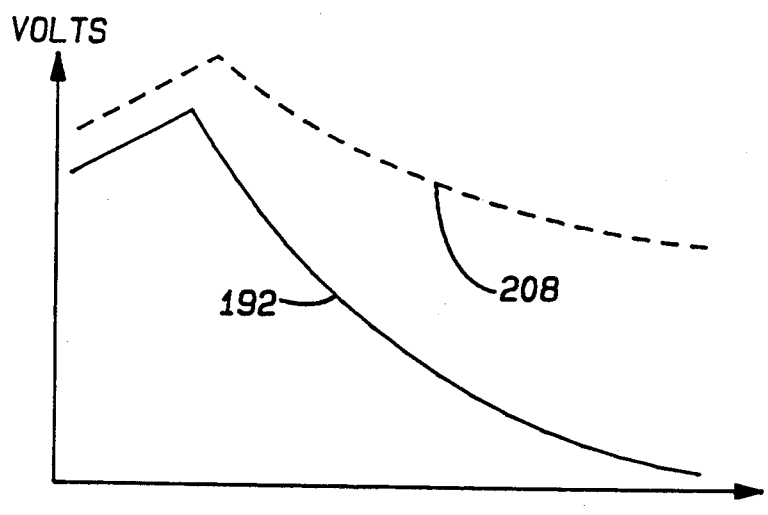
FIG. 22 shows a calibration bleed curve and an insitu bleed curve used to demonstrate one method of drift correction according to the present invention.

FIG. 22 depicts the calibration bleed curve 192 and an insitu bleed curve 208 which and will be used to demonstrate one method for drift correction. Insitu bleed curve 208 reflects drift in both vertical and horizontal directions as well as having a shape differing from calibration curve 192 in accordance with a gain change. As an initial point, with respect to curve 190 as depicted in FIG. 17, in practice the contact point 191 is extrapolated because the output voltage is discretely sampled at predetermined increments which are not assured of corresponding with $V_{max}$. Refering to FIG. 23, in order to estimate the contact point 214, the data points corresponding to the highest points for each of the upward 210a and downward 210b sloping portions of the curve are overlooked, and a substantially straight line is extrapolated based upon the next two highest data points collected for each of the upward 212a and downward 212b sloping portions of the curve. The point of intersection 214 of extrapolated upward 213a and downward 213b sloping lines is determined to be the contact point for the calibration curve depicted in FIG. 23.

Figure 23:
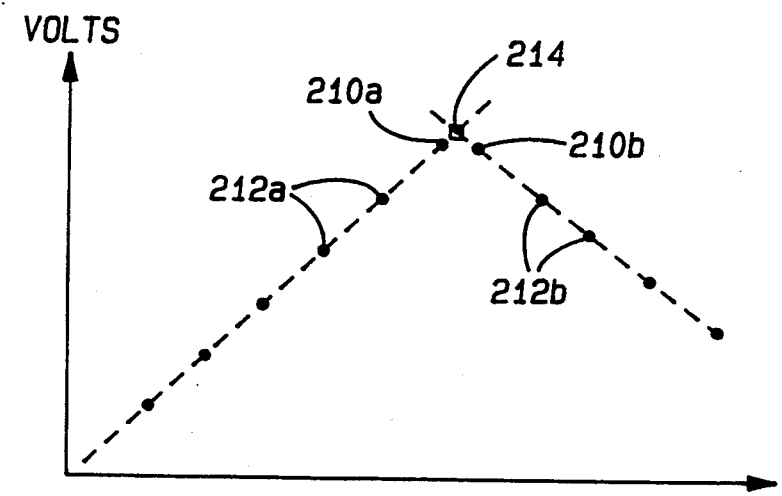
FIG. 23 is a graph illustrating the extrapolation of data points used to determine the contact point for the calibration curve.
Figure 24:
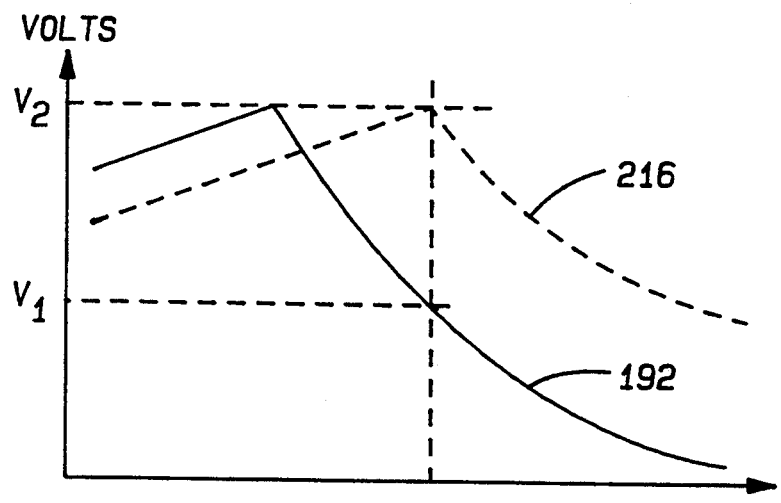
FIG. 24 shows an insitu bleed curve and a calibration bleed curve as used to determine external calibration and insitu calibration for determining the external pressure exhibited on the diaphragm when the insitu calibration bleed curve data is collected.

When catheter tip 160 is located in a body cavity, defined as insitu, insitu calibration occurs by first acquiring an insitu bleed curve 216 as shown in FIG. 24 in a manner similar to that used to obtain the calibration bleed curve 192 depicted in FIGS. 18 and 23. This requires the bleed process to be substantially repeatable, implying that the system time constant and initial pressure remain substantially the same so that the exponential decay of the bleed curves is substantially repeatable. The time constant is based on the physical parameters of the system such as pneumatic volume and orifice size and should not change. Initial pressure is set to the same value and verified using reference pressure transducer 134 of FIG. 13. Furthermore, the bleed process must occur within a time period during which the external pressure exerted on diaphragm 176 appears to be constant. External pressure changes occurring during data collection result in variation in the bleed curve by an unknown factor and make accurate calibration much less probable.

Referring to FIG. 24, external pressure exerted on diaphragm 176 is determined in accordance with a vertical shift of the insitu bleed curve 216 with respect to the calibration bleed curve 192. The external pressure is defined as the difference in pressure represented by voltage along the calibration bleed curve at the times when diaphragm 176 makes contact with mechanical stop 192 during external calibration $V_2$ and during insitu calibration $V_1$. The difference between the two voltages $V_1$ and $V_2$ along calibration bleed curve 192 represents the external pressure exerted upon diaphragm 176 when the insitu calibration bleed curve data is collected. Because accurate calculation of external pressure during the collection of bleed data improves when the data points are continuous, rather than discrete, data points, a continuous curve may be generated using any of a number of known curve fit algorithms. An improved continuous curve may also be provided by increasing the sample speed of the system.

Figure 25:
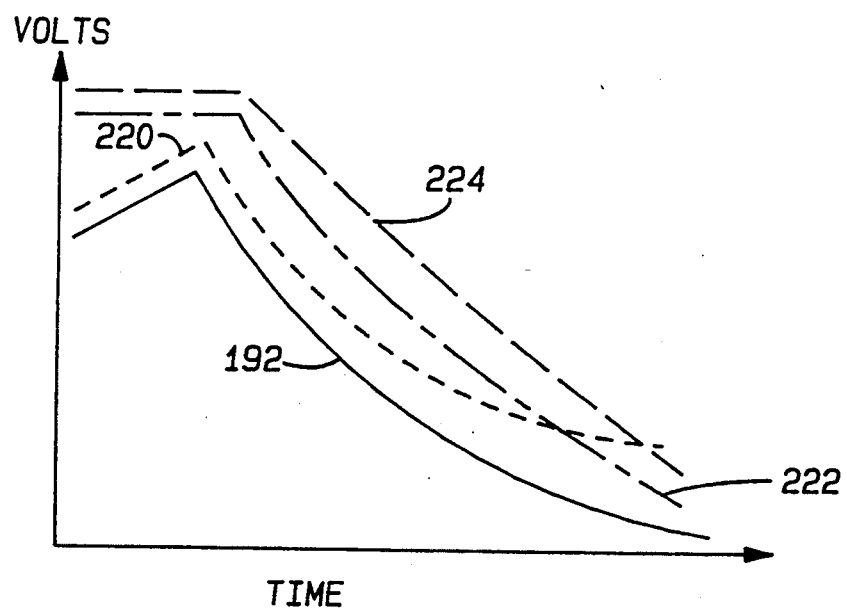
FIG. 25 shows the various curves used to generate a compensated pressure curve which is in turn used to determine an expected insitu bleed curve.

Referring now to FIG. 25, in order to determine an expected insitu bleed curve, it is first necessary to convert the calibration bleed curve 192 from units of output voltage to pressure using a table calculated during external calibration based on the curve of FIG. 17. Waveform 222 represents pressure versus catheter signal (in volts) of calibration curve 192 after conversion, but is superimposed onto FIG. 25 for purposes of explanation. Waveforms 222 and 224 actually have a horizontal axis representing pressure and vertical axis representing voltage. After conversion to units of pressure yielding converted pressure waveform 222, the external pressure calculated with respect to FIG. 23 is added to each point of converted pressure waveform 222 to yield a compensated pressure curve 224. The compensated pressure curve 224 is then converted from units of pressure to output signal voltage to yield an expected insitu bleed curve 220. The expected insitu bleed curve 220 is thus a measure of calibration curve 192 converted to units of pressure (converted pressure waveform 222) with the external pressure as determined above added to the calibration curve (compensated pressure curve 224), then converted back to units of output signal voltage. The difference between calibration bleed curve 192 and expected insitu bleed curve 220 at a particular time yields correction data, representatable in a curve similar to that depicted in curve 202 of FIG. 20, in units of output signal voltage which must be added to the measured output signal voltage when a pressure measurement is taken. In practice, a correction factor is determined at a number of discrete points along the curve. At each discrete point, two data points are noted. The first data point is the output signal value from the insitu bleed curve, and the second data point is the difference between the expected and the calibration bleed curves, the correction data. By fitting curves between each set of discrete points, a substantially continuous curve may be obtained. Extrapolation of this curve allows for correction of pressures below the external pressure at the time of calibration.

The calibration data is used in the following manner. When a pressure reading is taken, the output signal voltage for the pressure reading corresponds to the external pressure and any signal drift which may have occurred. During insitu calibration, the amount of signal drift is determined over an expected range of voltages using the insitu calibration method as described herein. At the particular signal voltage output during a pressure measurement, the expected signal voltage offset is added to the signal voltage output as a correction factor. This correction factor yields a corrected output voltage whose value may be used as an index into a calibration table whose values correspond to the original, external calibration curve as shown in FIG. 17 to determine the external pressure exerted on diaphragm 176. In this manner, the calibration method described herein provides more accurate measurements over a predetermined range of output voltages, and provides correction for temperature related, stress related and mechanically related drift.

While the above description constitutes the preferred embodiments of the present invention, it will be appreciated that the invention is susceptible of modification, variation and change without departing from the proper scope and fair meaning of the accompanying claims.

What is claimed is:

1. A fiber optic pressure sensor system for measuring pressure in a physical system, comprising:

an optical fiber having a sensing tip at a first end containing a pressure-sensitive diaphragm having an inner surface facing said optical fiber first end and an outer surface, said diaphragm positioned beyond said first end of said fiber, said diaphragm modulating a pressure-sensing light signal injected into the opposite second end of said optical fiber and returning a light signal of varying intensity into said fiber, said sensing tip further containing a contacting surface for engaging said diaphragm upon application of a pressure differential between said diaphragm inner and outer surfaces;

drift correcting means for providing a correction signal applied to said pressure-sensing light signal, said correction signal compensating for drift in said pressure-sensing light signal, said drift correcting means including pressure applying means for causing a time-varying level of pressure differential to act across said surface of said diaphragm providing a pressure sweep to cause said diaphragm to contact said contacting surface to define a contact event and detection means for detecting the value of said differential and detecting said pressure-sensing light signal upon said contact event, pressure-sensing light signal as said intensity varies in accordance with said pressure said correction signal determined in accordance with the difference in the values of said pressure-sensing light signal during said pressure sweep while said sensing tip is within said physical system and the values of said pressure-sensing light signal during a pressure sweep within said sensing tip outside said physical system;

optical means for injecting said pressure sensing light signal into said fiber second end and for receiving said returned light signal; and signal processing means for interpreting said light pressure sensing signal modulated by said pressure sensitive element.

2. The fiber optic pressure sensor of claim 1 wherein said pressure means comprises a pump applying a vacuum to said inner surface of said pressure-sensitive diaphragm.

3. The fiber optic pressure sensor of claim 1 wherein said pressure sensing tip includes a ferrule containing said optical fiber, said ferrule having an angle polish to define two faces on said ferrule having an angle polish to define two faces on said ferrule having an angle polish to define two faces on said ferrule, one face being substantially perpendicular to an imaginary longitudinal axis of said optical fiber, the other face including said optical fiber and forming an angle with said first face, said first and second faces intersecting to define an end stop contactable with said diaphragm when said pressure means has applied a sufficient level of pressure differential to said diaphragm, said intersection modifying the character of said pressure-sensing signal when said diaphragm makes contact with said fiber.

4. The fiber optic pressure sensor of claim 1 wherein said pressure means applies a temporally-linear vacuum pressure function, said pressure function further containing a time-varying, periodic pressure function with an associated dithering frequency superimposed on said linear pressure function.

5. The fiber optic pressure sensor of claim 4 wherein said dithering frequency is chosen to be above the range of pressure frequencies of interest in said physical system.

6. The fiber optic pressure sensor of claim 5 wherein said dithering frequency is chosen to be above 50 Hertz.

7. The fiber optic pressure sensor of claim 1 wherein said physical system is the body of a living organism.

8. The fiber optic sensor of claim 1 wherein said pressure sweep includes application of a vacuum pressure to said inner surface of said diaphragm followed by pressure release.

9. The fiber optic pressure sensor of claim 8 wherein said pressure release occurs at a constant rate.

* * * * *

UNITED STATES PATENT AND TRADEMARK OFFICE
CERTIFICATE OF CORRECTION

PATENT NO. : 5,422,478
DATED : June 6, 1995
INVENTOR(S) : Marek T. Wlodarczyk
David O. Danielson It is certified that error appears in the above-indentified patent and that said Letters Patent is hereby corrected as shown below:

Column 15, line 40, Claim 1, after "said" delete "differential and detecting said".

Column 15, line 40, Claim 1, after "signal" delete "upon said contact event, pressure-sensing light signal".

Column 15, line 43, Claim 1, after "pressure" insert --differential and detecting said pressure-sensing light signal upon said contact event,--.

Signed and Sealed this

Eleventh Day of June, 1996

Attest:

BRUCE LEHMAN

Attesting Officer

Commissioner of Patents and Trademarks